United States Patent
Ganton et al.

(10) Patent No.: US 11,406,288 B2
(45) Date of Patent: Aug. 9, 2022

(54) ACTIVITY MONITORING VIA ACCELEROMETER THRESHOLD INTERRUPT METHOD

(71) Applicant: PHILIPS HEALTHCARE INFORMATICS, INC., Cambridge, MA (US)

(72) Inventors: Robert Ganton, San Diego, CA (US); Robert Ballam, Eatons Hill (AU)

(73) Assignee: PHILIPS HEALTHCARE INFORMATICS, INC., Cambridge, MA (US)

( * ) Notice: Subject to any disclaimer, the term of this patent is extended or adjusted under 35 U.S.C. 154(b) by 0 days.

(21) Appl. No.: 15/669,513

(22) Filed: Aug. 4, 2017

(65) Prior Publication Data

US 2018/0192921 A1    Jul. 12, 2018

Related U.S. Application Data

(60) Provisional application No. 62/443,424, filed on Jan. 6, 2017.

(51) Int. Cl.
| | |
|---|---|
| *A61B 5/11* | (2006.01) |
| *A61B 5/00* | (2006.01) |
| *A61B 5/0205* | (2006.01) |
| *G01P 13/00* | (2006.01) |
| *A61B 5/024* | (2006.01) |
| *A61B 5/08* | (2006.01) |
| *A61B 5/0533* | (2021.01) |

(52) U.S. Cl.
CPC .......... *A61B 5/1118* (2013.01); *A61B 5/002* (2013.01); *A61B 5/7271* (2013.01); *A61B 5/024* (2013.01); *A61B 5/0205* (2013.01); *A61B 5/0533* (2013.01); *A61B 5/0816* (2013.01); *A61B 5/6832* (2013.01); *A61B 2562/0219* (2013.01); *G01P 13/00* (2013.01)

(58) Field of Classification Search
CPC ..... A61B 5/1118; A61B 5/002; A61B 5/7271; A61B 5/0205; A61B 5/024; A61B 5/0533; A61B 5/0816; A61B 5/6832; A61B 2562/0219; G01P 13/00
USPC ......................................... 600/301, 535, 595
See application file for complete search history.

(56) References Cited

U.S. PATENT DOCUMENTS

| | | | | |
|---|---|---|---|---|
| 6,997,882 | B1 * | 2/2006 | Parker | A61B 5/08 600/301 |
| 8,206,325 | B1 * | 6/2012 | Najafi | A61B 5/1117 600/595 |
| 8,244,200 | B2 * | 8/2012 | Orr | G06F 1/3203 455/343.1 |
| 9,146,605 | B2 * | 9/2015 | Lee | G06F 1/163 |
| 9,220,410 | B2 * | 12/2015 | Sheynblat | A61B 5/021 |
| 9,345,433 | B1 * | 5/2016 | Shinozuka | H05K 7/12 |

(Continued)

*Primary Examiner* — Carl H Layno
*Assistant Examiner* — Michael J Lau

(57) ABSTRACT

Methods, systems, computer-readable media, and apparatuses for determining a sedentary state of a user are disclosed. The apparatuses can be fastened to the user and include sensors configured to detect movement of the user. The apparatuses can also include a circuit coupled to the sensors. The circuits may be configured to determine, using the sensors, whether the user is sedentary; and in response to determining that the user is sedentary, determine one or more physiological attributes of the user of the device.

33 Claims, 6 Drawing Sheets

(56) References Cited

U.S. PATENT DOCUMENTS

| | | | | |
|---|---|---|---|---|
| 9,504,408 B2* | 11/2016 | Hong | | A61B 5/1123 |
| 2002/0151824 A1* | 10/2002 | Fischer | | A61B 5/103 |
| | | | | 600/595 |
| 2004/0102931 A1* | 5/2004 | Ellis | | A61B 5/0205 |
| | | | | 702/188 |
| 2006/0084848 A1* | 4/2006 | Mitchnick | | A61B 5/411 |
| | | | | 600/595 |
| 2008/0077055 A1* | 3/2008 | Allen | | A61B 5/1118 |
| | | | | 600/595 |
| 2008/0167535 A1* | 7/2008 | Stivoric | | G01K 1/02 |
| | | | | 600/301 |
| 2010/0217533 A1* | 8/2010 | Nadkarni | | G16H 50/20 |
| | | | | 702/19 |
| 2011/0066064 A1* | 3/2011 | Jangle | | A61B 5/6822 |
| | | | | 600/534 |
| 2012/0029318 A1* | 2/2012 | Kuo | | A61B 5/318 |
| | | | | 600/301 |
| 2013/0015976 A1* | 1/2013 | Chang | | A61B 5/4561 |
| | | | | 340/573.7 |
| 2013/0035562 A1* | 2/2013 | Besko | | A61B 5/6838 |
| | | | | 600/301 |
| 2013/0106684 A1* | 5/2013 | Weast | | G04G 17/06 |
| | | | | 345/156 |
| 2013/0162423 A1* | 6/2013 | Rowe | | A61B 5/1115 |
| | | | | 340/501 |
| 2013/0207889 A1* | 8/2013 | Chang | | G01P 15/00 |
| | | | | 345/156 |
| 2013/0274565 A1* | 10/2013 | Langer | | A61B 5/0205 |
| | | | | 600/301 |
| 2014/0174174 A1* | 6/2014 | Uehara | | A61B 5/4519 |
| | | | | 73/379.01 |
| 2014/0278229 A1* | 9/2014 | Hong | | A61B 5/486 |
| | | | | 702/160 |
| 2015/0057967 A1* | 2/2015 | Albinali | | A61B 5/1118 |
| | | | | 702/150 |
| 2015/0106052 A1* | 4/2015 | Balakrishnan | | G06F 3/011 |
| | | | | 702/150 |
| 2015/0313535 A1* | 11/2015 | Alshaer | | A61B 5/0816 |
| | | | | 600/529 |
| 2015/0346824 A1* | 12/2015 | Chen | | H04N 5/4403 |
| | | | | 345/156 |
| 2015/0374267 A1* | 12/2015 | Laughlin | | A61B 5/1118 |
| | | | | 702/19 |
| 2016/0038093 A1* | 2/2016 | Sharma | | A61B 5/7278 |
| | | | | 600/481 |
| 2016/0112668 A1* | 4/2016 | Schafer | | H04N 21/44222 |
| | | | | 348/734 |
| 2016/0150989 A1* | 6/2016 | Felix | | A61B 5/0006 |
| | | | | 600/523 |
| 2016/0198995 A1* | 7/2016 | Yeung | | A61B 5/6826 |
| | | | | 600/595 |
| 2016/0203691 A1* | 7/2016 | Arnold | | A61B 5/7264 |
| | | | | 340/539.12 |
| 2016/0213263 A1* | 7/2016 | Felix | | A61B 5/1118 |
| 2016/0262693 A1* | 9/2016 | Sheon | | A61B 5/4866 |
| 2016/0307427 A1* | 10/2016 | Haflinger | | G08B 21/0446 |
| 2016/0310329 A1* | 10/2016 | Patel | | A61B 5/1118 |

* cited by examiner

ACTIVITY MONITORING VIA ACCELEROMETER THRESHOLD INTERRUPT METHOD

CROSS-REFERENCES TO RELATED APPLICATIONS

This patent application claims priority to U.S. Provisional Patent Application Ser. No. 62/443,424, filed Jan. 6, 2017, entitled "ACTIVITY MONITORING VIA ACCELEROMETER THRESHOLD INTERRUPT METHOD," which is assigned to the assignee hereof and is incorporated herein by reference in its entirety for all purposes.

BACKGROUND

Aspects of the disclosure relate to activity monitors.

Measurements corresponding to a level of activity of a person can be used in a variety of manner to assess health. Certain activity monitoring devices can be worn by a user to measure whether the user has moved in order to assess a level of activity. However, such devices can be incapable of determining whether a user is sedentary, an activity level of a user over extended periods of time, and/or may be prohibitively expensive or cumbersome. As such, there is need for improvement in the field of activity monitoring devices.

BRIEF SUMMARY

Certain embodiments are described that provide techniques corresponding to a device including a fastener configured to attach the device to a user of the device. The device can include a sensor coupled to the fastener. The sensor can be configured to detect whether the user has moved. The device can include a circuit coupled to the sensor. The circuit can be configured to determine, using the sensor, whether the user is sedentary and in response to determining that the user is sedentary, determine one or more physiological attributes of the user of the device. Determining whether the user is sedentary can include determining whether a movement of the user detected by the sensor is within a threshold movement amount determined to indicate that the user is sedentary.

Determining whether the user is sedentary can include summing several movements over a time period to determine whether a resulting summation exceeds a corresponding threshold. The sensor can include an accelerometer or a gyroscope configured to detect whether the user has moved. Determining that the user is sedentary can include determining that a magnitude of a translational or rotational force detected by the sensor corresponding to movement of the user has not met a threshold value. The sensor can be configured to detect a combination of rotational or translational forces to determine whether a certain movement of the user has not been performed. The circuit can be configured to determine, using the sensor, that the certain movement of the user has not been performed. Determining the one or more physiological attributes can include performing one or more measurements on the user.

The one or more physiological attributes can include a heart rate, a breathing rate, or galvanic skin response of the user. Performing the one or more measurements can include inducing one or more sensors to enter a high power state from a low power state. The device can include the one or more sensors. The circuit can be configured to, in response to determining that the user is sedentary, determine a length of time that the user has been sedentary. The circuit can be configured to operate selectively in a low power state and a high power state, wherein the circuit is unable to determine whether the user is sedentary in the low power state. The circuit can also be configured to periodically enter the high power state from the low power state to sample readings from the sensor to determine whether the user is sedentary.

The sensor can be configured to, in response to determining that a sensor reading corresponding to movement of the user meets a threshold value, set an interrupt to a first state. Determining that the user is sedentary can include, by the circuit, while in the high power state, determining whether the interrupt is in the first state. The circuit, upon determining that the interrupt is in the first state, can set the interrupt to a second state and enter the low power state.

Determining that the user is sedentary can include determining that a sensor reading indicative of movement of the user has not exceeded a threshold value for a period of time. The fastener can include an adhesive to enable joining of the device to the user. The device can include a power source coupled to the sensor and the circuit and a housing coupled to the sensor, the circuit, and the power source. The housing can be configured to prevent access to the power source without destructive deformation of the housing. The device can include a transmitter coupled to the circuit. The circuit can be configured to transmit data, via the transmitter. The data can be indicative of a sedentary state of the user. The transmitter can be a Bluetooth® or NFC® compliant transmitter. The device can include a memory configured to store data indicative of several discontinuous periods of time that the user has been sedentary. The data transmitted via the transmitter can includes the data indicative of several discontinuous periods of time that the user has been sedentary. The data indicative of several discontinuous periods of time that the user has been sedentary can include times of day corresponding to each of the several discontinuous periods of time.

BRIEF DESCRIPTION OF THE DRAWINGS

Aspects of the disclosure are illustrated by way of example. In the accompanying figures, like reference numbers indicate similar elements.

DETAILED DESCRIPTION

Figure 1:
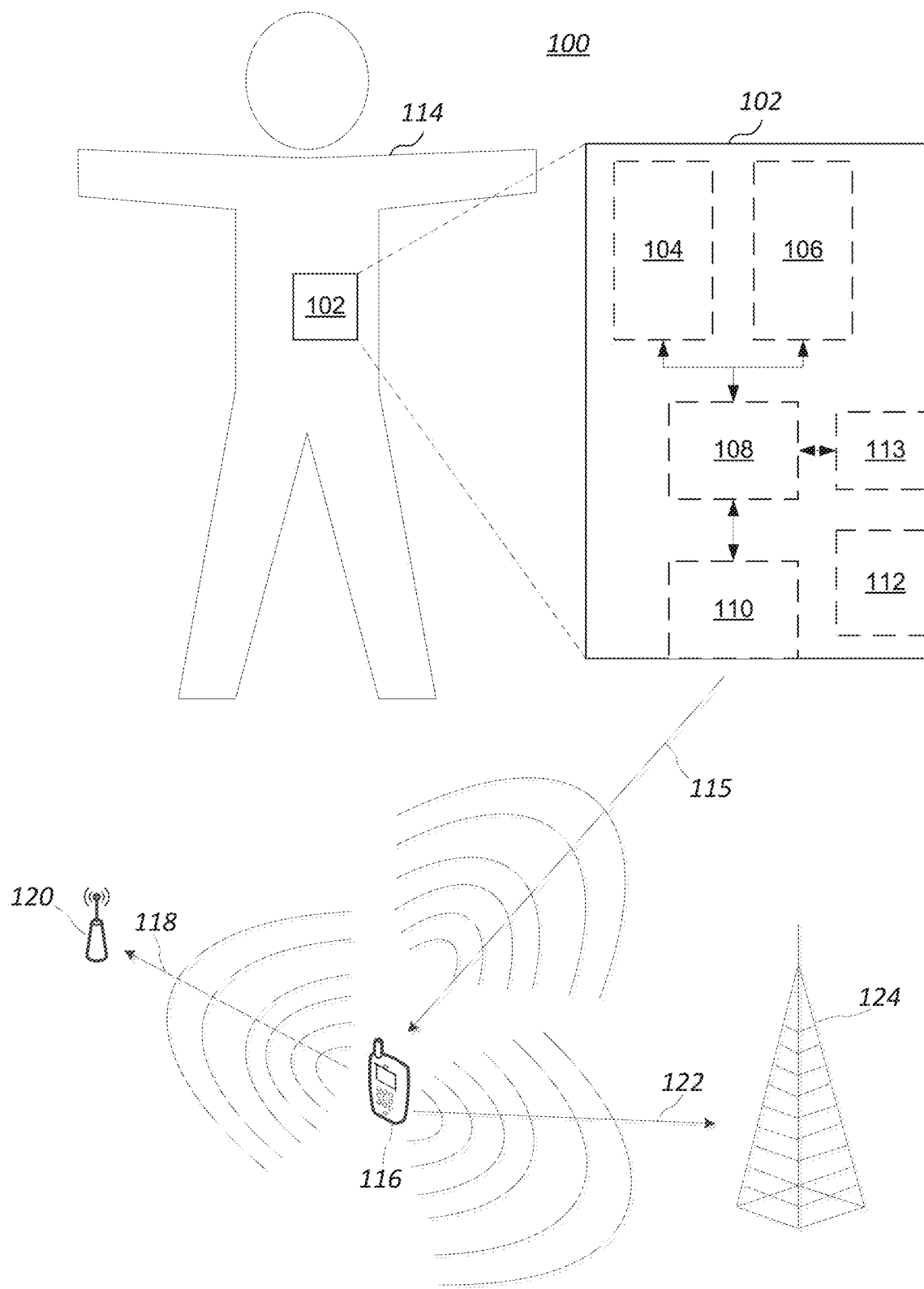
FIG. 1 illustrates a simplified diagram of a system that may incorporate one or more embodiments including a medical device coupled to a user to determine an activity level of the user.

Several illustrative embodiments will now be described with respect to the accompanying drawings, which form a part hereof. While particular embodiments, in which one or more aspects of the disclosure may be implemented, are described below, other embodiments may be used and various modifications may be made without departing from the scope of the disclosure or the spirit of the appended claims.

Disclosed are techniques for implementing device(s) that can be used determine whether a user is sedentary using a low-cost and/or unobtrusive device that can be attached to the user. A sedentary user can be user that is relatively inactive for a period of time. A sedentary status of a user can indicate that the user is in poor or deteriorating health. Sedentary users may have physical or psychological issues preventing them from perform physical activities to maintain or improve their health. Determination of whether a user is sedentary using a device attached to the user can present several challenges. For example, it may be difficult for such a device to remain coupled to the user without presenting discomfort or annoyance. Furthermore, it may be difficult for such a device to operate for extended periods of time that may be necessary to determine if a user is sedentary and/or sufficient information to determine information related to sedentary periods of a user with sufficient granularity.

In certain embodiments, certain physiological attributes of a user can be determined in response to determining that the user is in a sedentary state. For example, a heart rate, breathing rate, galvanic skin response, or other physiological attributes may be measured. When a user is sedentary, determination of such physiological attributes may be relatively easier to determine via a disclosed device. For example, less power may be needed to determine, analyze, and/or filter sensor data used to determine a physiological attribute. An accelerometer used to measure a breathing rate, for example, may encounter relatively less movement noise when a user is sedentary as compared to when a user is active. A sensor, circuit, or accompanying components used to determine a physiological attribute may also be less accurate, sensitive, lower cost, and/or use lower power to determine physiological attributes when a user is sedentary because, for example, a lower signal-to-noise ratio may be more tolerable when a user is sedentary to determine a physiological attribute as compared to when a user is active. In certain embodiments, a user may be sedentary when they are asleep, for example. Physiological attributes may determine when the user is asleep and used to infer health information about the user while the user is sleeping (such as a quality of sleep, a resting heart rate, etc.).

In certain embodiments, a device can be configured to be attached to a user as a medical patch and/or in close proximity to a user (e.g., attached to a belt, wrist, necklace, etc.). The device can be configured to be a one-time use/disposable device and can include one or more sensors, processors, or power sources disposed within a housing. The housing can be configured to require destructive deformation of the housing to gain access to components disposed therein in order to prevent harm to the user and/or to minimize device manufacturing costs. The housing can be attached to a user via an adhesive patch or other fastener. Furthermore, the device can be relatively compact, lightweight, and/or low-cost.

The techniques disclosed can utilize a device including an accelerometer or similar sensor that can be configured to determine movement(s) of a user to which the device is attached. As the user moves, the sensor can be used to detect the movement. A level of activity of the user can be determined over time period(s) by examining magnitude(s) of forces detected by the sensor in response to the user moving over the time period(s). Disclosed techniques can be used to implement devices that can be coupled to a user to determine if the user is sedentary. The devices can be relatively compact, light, and low-cost by minimizing power consumption to implement movement determination features of the device. The devices disclosed herein can be relatively light weight and compact so that the devices can be comfortably worn by a user without obstructing the user's normal day to day activities. The devices can include a circuit that can selectively operate in a lower power state and a high power state. While in the low power state, the circuit can power gate, reduce voltage, reduce frequency, disable functionality, or perform other actions to reduce power consumption of the circuit. For example, the circuit can enter a sleep state wherein functionality of the circuit is limited. While in the high power state, the functionality of the circuit can be enabled corresponding to increased power consumption of the circuit.

Disclosed devices can include an accelerometer, gyroscope, or similar sensor. When the device is coupled to a user, force(s) measured by the sensor can correspond to movement by the user (e.g., the disclosed devices may move in response to a movement by a user of the device). In certain embodiments, the sensor can operate independently from the controller. When the sensor determines that a measured force exceeds a threshold, an interrupt or similar signal or register value can be set to a first set. The circuit can be configured to periodically enter a high power state from a low power state. While in the high power state, the circuit may be capable of performing actions that the circuit may be incapable of performing in the low power state. For example, while in the high power state, the circuit may be able to determine a state of the interrupt, log information pertaining to the user's activity level, transmit such information to another device, perform additional measurements, activate other devices, etc.

The circuit can be configured to, upon waking up from the low power state, determine whether the interrupt is set to the first state (indicating that a sensor measurement has met a threshold indicating that the user has been relatively active) or that the interrupt has not been set to the first state (indicating that the user has been relatively sedentary for an amount of time that the circuit was in the low power state). If a state of the interrupt indicates that the threshold was met, the controller can proceed to enter the low power state again or, in certain embodiments, activate one or more additional sensors. The additional sensors can, in certain embodiments, be activated to gather information regarding the user when the user is likely to be sedentary. For example, sensor(s) to generate an electrocardiogram for the user or gather heart rate or respiration rate information of the user may be more accurate when the user is sedentary. The circuit can activate the additional sensors to gather information regarding the user for a time after it is determined that the interrupt indicates that the threshold was not met (e.g., that the user is sedentary). In certain embodiments, sedentary periods of the user can be determined over time and used to predict a likely future time period when the user is likely to be sedentary.

In certain embodiments, an active or sedentary state of a user can be determined without use of an interrupt. For example, a sensor signal can be directly compared to a threshold value for the signal wherein the threshold is used to determine whether the user is sedentary. The circuit may or may not selectively operate in a lower power and high power state when utilizing the sensor to determine a sedentary state of the user.

If the state of the interrupt indicates that the threshold was met (indicating that the user has been or is active), the circuit can perform one of several actions. For example, the circuit may reset the state of the interrupt and re-enter a low-power state to await a future time period when the user is likely to be sedentary. The circuit may log data indicating a length of time that a user was sedentary (e.g., a length of time that the threshold was not met). The circuit can activate one or more additional sensors to gather more information that can be used to further assess a level of activity of the user or other health information pertaining to the user. The circuit can transmit logged data to an external device, such as a smartphone or other device, using a relatively low power data transfer interface so that the external device can upload the data to a cloud, for example, and/or perform operations on the data.

By periodically awaking from a low power state, instead of continuously operating in a high power state, power consumption of a device including the circuit can be minimized. In certain embodiments, power consumption of an activity monitoring device can be decreased from approximately 100 µA to approx. 1-5 µA. Decreasing the power consumption can enable an activity monitoring device to be relatively compact and light weight to be worn by a user, and can be implement as a patch. Furthermore, cost of the device can be minimized. For example, a size and/or cost power supply needed to power such a device for a target amount of time can be minimized.

Techniques of the disclosure can be used to determine an activity level (e.g., whether a user is sedentary) of a user over extended periods of time (such as over several days, weeks, or months) using a single, low-cost, and/or disposable device coupled to the user. The device can be used to determine if a user is substantially sedentary (e.g., has an excessively low level of activity) that can indicate that the user is in poor health. Such information may otherwise be difficult to obtain as the user may not necessarily be aware of their level of activity, may not tolerate a larger or more obtrusive device, or a devices may be prohibitively expensive.

FIG. 1 illustrates a system 100 that can include several features of the disclosure. Illustrated is a device 102, that can include a fastener (not shown) that can be used to mechanically couple device 102 in proximity to user 114. For example, device can be worn as a patch (via an adhesive), on a necklace, on a belt, on a wristband, etc. in close proximity to a user 114. The fastener can be configured such that device 102 moves in response to a corresponding movement of user 114. Device 102 can include an sensor 104 or similar sensor operable to detect movement of user 114. Accelerometer 104 can be coupled to circuit 108, which can include a processor for example Circuit 108 can be configured to selectively operate in a high power state and a low power state. As disclosed herein, while in the lower power, certain functionalities of circuit 108 can be disabled in order to reduce power consumption of circuit 108. While in the high power state, the functionalities of circuit 108 can be enabled at the expense of requiring higher power consumption.

As disclosed herein, sensor 104 can be configured to set a state of an interrupt in response to sensor 104 determines that a sensed force meets a threshold. Circuit 108, in response to determining a state of the interrupt, can perform one or more actions. For example, circuit 108 may remain in a high power state and transmit information pertaining to inactivity of user 114, activate one or more additional sensor(s) 106, and/or return to a low power state. Additional sensor(s) 106 can include, without limitation sensors to determine pulse oximetry, respiration, pulse, temperature, etc. Controller can be coupled to memory 113. Memory 113 can, for example, store one or more instructions to configure circuit 108 and/or data populated by circuit 108 that can indicate a level of activity of user 114. Device 102 can also include power source 112 to power components(s) of device 102 disclosed herein. Power source 112 can be a battery or capacitor, for example, that may be configured to enable wireless (e.g., inductive) charging of power source 112.

Circuit 108 can be coupled to a transceiver 110 to enable wireless communication with mobile device 116. Mobile device 116 may be a device designed to perform numerous functions, including the ability to communicate, via a relatively long distance communication link, with a server (not shown). The server can collect activity information for user 114. In the example shown in FIG. 1, mobile device 116 is able to perform wireless communications by sending signals to, and receiving signals from, one or more base stations 120. For instance, mobile device 116 may send a communication signal 118 to an access point 120, which may be a base station supporting Wi-Fi® communications. Mobile device 116 may send a communication signal 122 to cell tower 124, which may be a base station supporting LTE® or other cellular communications. Communication signal 115 between device 102 and mobile device 116 can be relatively lower in power and/or range as compared to communication signals 118 and/or 122. For example, communication signal 115 can be a Bluetooth® or near field communication (NFC®) transmission. In certain embodiments, device 102 may be constrained with regards to cost, operating time requirement(s), weight, and/or size and therefore relatively high power consumption components and/or batteries necessary to support longer range communications may not be integrated into device 102.

Figure 2:
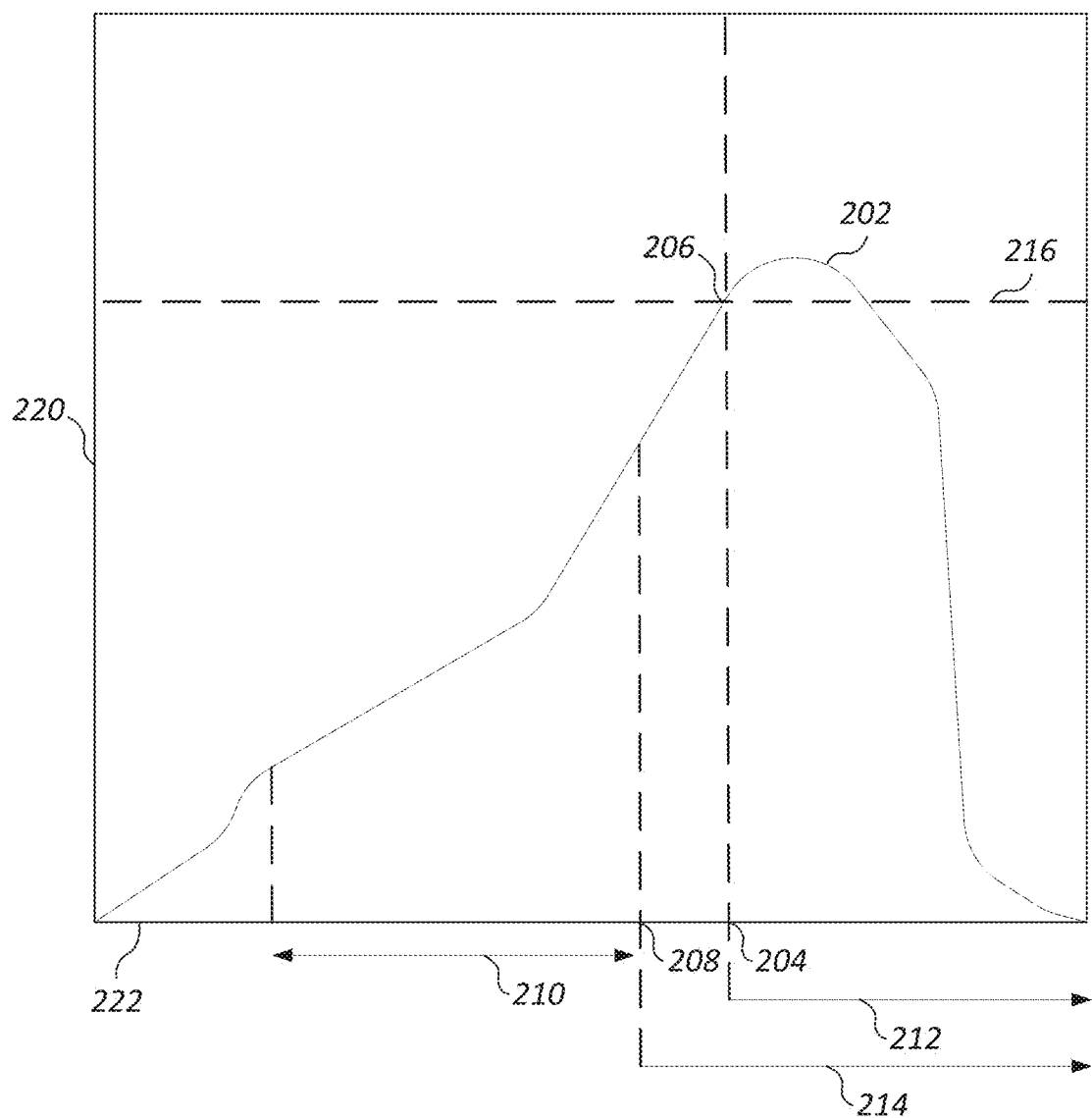
FIG. 2 illustrates an example graph for describing activity-level determination features of the disclosure.

FIG. 2 illustrates a graph 200 to illustrate features of the disclosure. Graph 200 illustrates a signal 202 representing force 220 sensed by sensor 104, for example, over time 222. As illustrated, a threshold 216 can be selected such that when signal 202 meets threshold 216 at point 206 (indicating that a corresponding force has met a threshold), an interrupt can be latched or otherwise set to a state by sensor 104 at time instance 204. Thus, during a time period indicated by arrow 212, the interrupt may be set to a first state. If the interrupt is sampled by a controller (such as circuit 108) during time period indicated by arrow 212, the controller can determine that threshold 216 has been met.

As another example, a threshold can include a time component such that force 202 can be integrated over a time period 210. As an example, a threshold can be met if the integration of signal 202 over a time period 210 meets a corresponding threshold. Such functionality can be implemented by, for example, a capacitor coupled to an accelerometer output that outputs signal(s) corresponding to detected force(s) as a linear function of output voltage. If the threshold is met, an interrupt can be latched at time instance 208 during a time period indicated by arrow 214.

Figure 3:
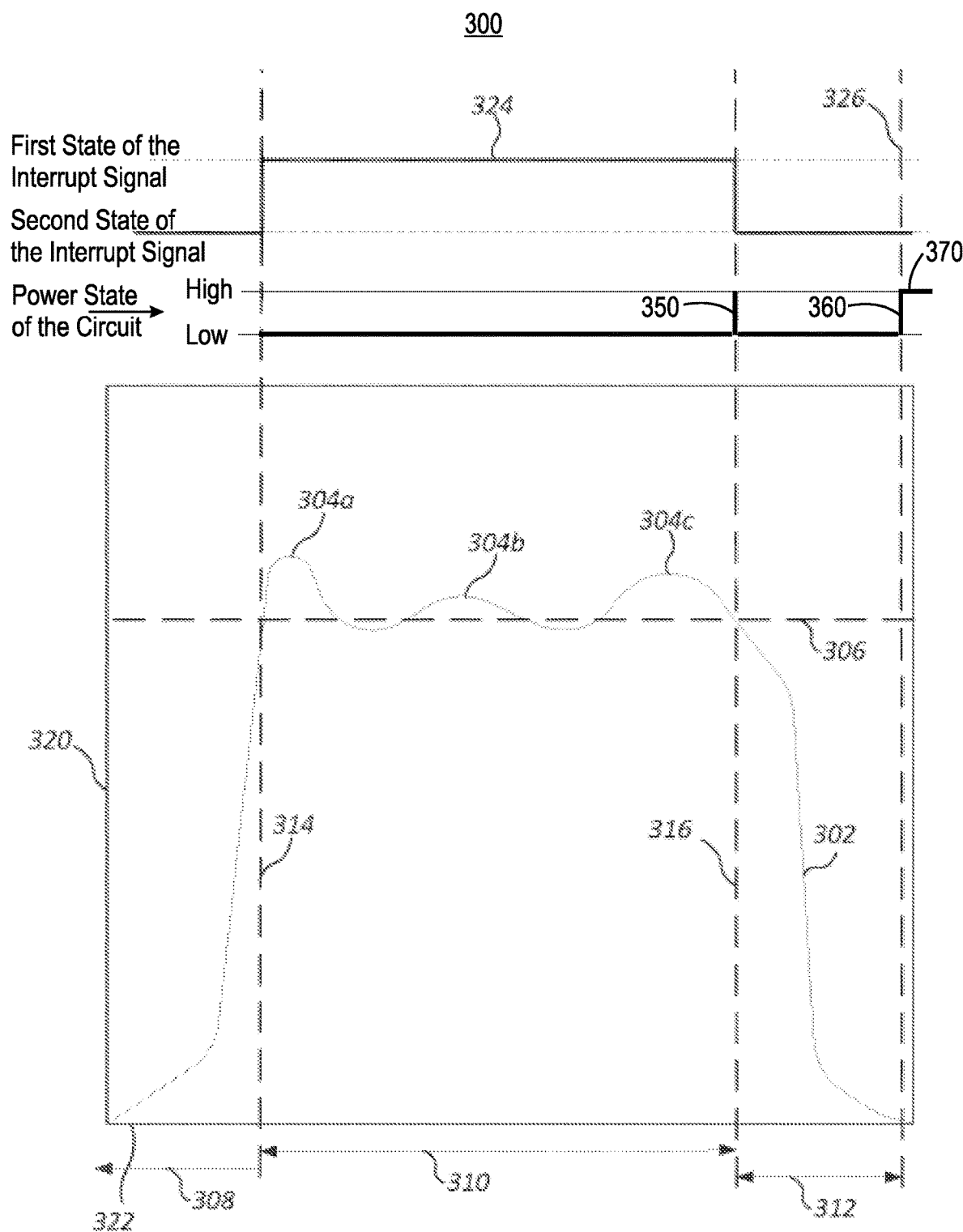
FIG. 3 illustrates an example graph for describing activity-level determination features of the disclosure.

FIG. 3 further illustrates graph 300 that can represent a magnitude 320 of a signal 302 over time 322 representative of a force sensed to a disclosed device coupled to a user indicating movement of the user. Signal 302 may exceed threshold 306 at sections labeled 304a, 304b, and 304c. During time period 308, the user may be relatively sedentary as a signal generated corresponding to a movement of the user has not exceed threshold 306. At time 314, portion 304a of signal 302 is illustrated as exceeding threshold 306. Thus, at time 314, an interrupt can be set to a first state to indicate that the user may no longer be sedentary.

In certain embodiments, a user may be determined to not be sedentary during time period 310. At time 316, a circuit may enter a high power state at 350 and detect a state of interrupt 324 set by an accelerometer or other sensor. The circuit may reset interrupt signal 324 to a second state at time period 316, as illustrated. At time 326, the circuit may again enter the high power state at 360 and check a state of interrupt 324 to determine whether a user has been sedentary. As illustrated, if signal 302 does not exceed threshold 306 during time period 312, then the circuit may determine that a user has been sedentary during time period 312. If a user is sedentary during time period 312, then the circuit may remain in a high power state following time period 326 at 370 to perform one or more measurements, analyses, or data transfer(s) pertaining to physiological attributes of a user. In certain embodiments, time 326 may be analyzed with respect to historic activity level vs time values (e.g., a user may be consistently inactive during certain times) to determine whether a user is more likely to be inactive following time 326.

In certain embodiments, a time component may be utilized as well as a magnitude of a signal to determine whether a user has been active or sedentary. For example, portions 304a, 304b, and 304c each exceed threshold 306. However, portions of signal 302 also not exceed threshold 306 during time period 310. However, signal 302 may be integrated or otherwise analyzed during time period 310 to determine whether a user has been sedentary during time period 310. Thus, portions 304a, 304b, and 304c can, as a whole, by analyzed to determine that a user has been active or sedentary during time period 310 instead of each of portions 304a, 304b, and 304c being individually analyzed (e.g., via a binary crosses threshold/does not cross threshold determination).

Figure 4:
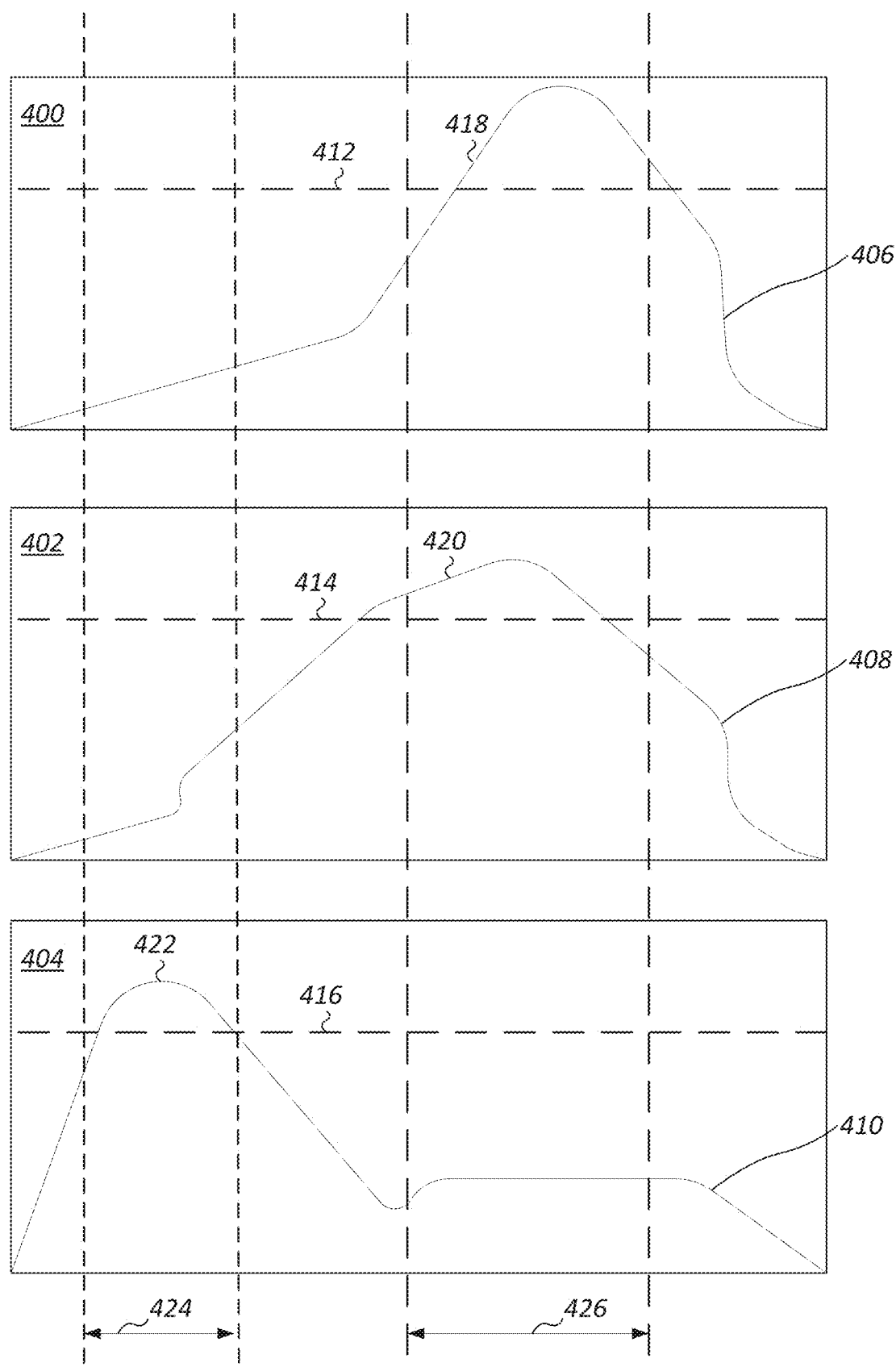
FIG. 4 illustrates example graphs for describing activity-level determination features of the disclosure.

FIG. 4 illustrates several graphs 400, 402, and 404 that can each illustrate a representation of a signal output by a sensor (or a physical attribute detected by a corresponding sensor). For example, each of graphs 400, 402, and 404 can represent a translational force, rotational force, force in a certain direction/orientation, etc., in any combination. In certain embodiments, a multi-axis accelerometer and/or gyroscope may be used to determine whether a user is sedentary. Each of graphs 400, 402, and 404 may correspond to a respective axis (e.g., translational or rotational).

As illustrated, each of graphs 400, 402, and 404 may include a respective one of signals 406, 408, and 410 and a respective one of thresholds 412, 414, and 416. In certain embodiments, combinations of signals 406, 408, and 410 can be analyzed at points in time or over time periods to determine whether a user is or has been sedentary. For example, during time period 424, a determination can be made that a user has been sedentary because, although portion 422 of signal 410 has exceeded threshold 416, signals 406 and 408 have not exceeded respective thresholds 412 and 414 during time period 424. During time period 426, a user may be determine to be active because portion 418 of signal 406 exceeds threshold 412 and portion 420 of signal 408 exceeds 414 during time period 426 even though signal 410 does not exceed threshold 416.

An accelerometer may output a gravity vector as a result of gravity of the Earth being incident upon the accelerometer. In certain embodiments, the gravity vector can be removed from accelerometer measurements to determine a force incident upon the accelerometer as a result of a user movement. A high pass filter may be coupled to an accelerometer to filter signal component(s) corresponding to a gravity vector. The high pass filter may filter out signal component(s) that are constant, such as signal component(s) of the gravity vector In certain embodiments, thresholds 412, 414, and 416 can each be selected depending on a corresponding orientation/axis of movement that may be more or less indicative of a movement of a user. For example, a sensor value corresponding to movement of an appendage of a user may have a different threshold as compared to a sensor value corresponding to movement of a head of a user. In certain embodiments, a certain movements of a user may be targeted to determine if a certain movement/part of the user is sedentary. For example, a determination can be made that a right leg of a user has been sedentary to verify that the user has not used the right leg against the advice of a medical practitioner.

Although FIGS. 2-4 have been discussed with regards to time periods, sensor values can be analyzed with respect to frequency, other domains, or in any combination. For example, an amplitude of a signal within a frequency domain may be compared to a corresponding threshold to determine if a user has been sedentary or not.

Figure 5:
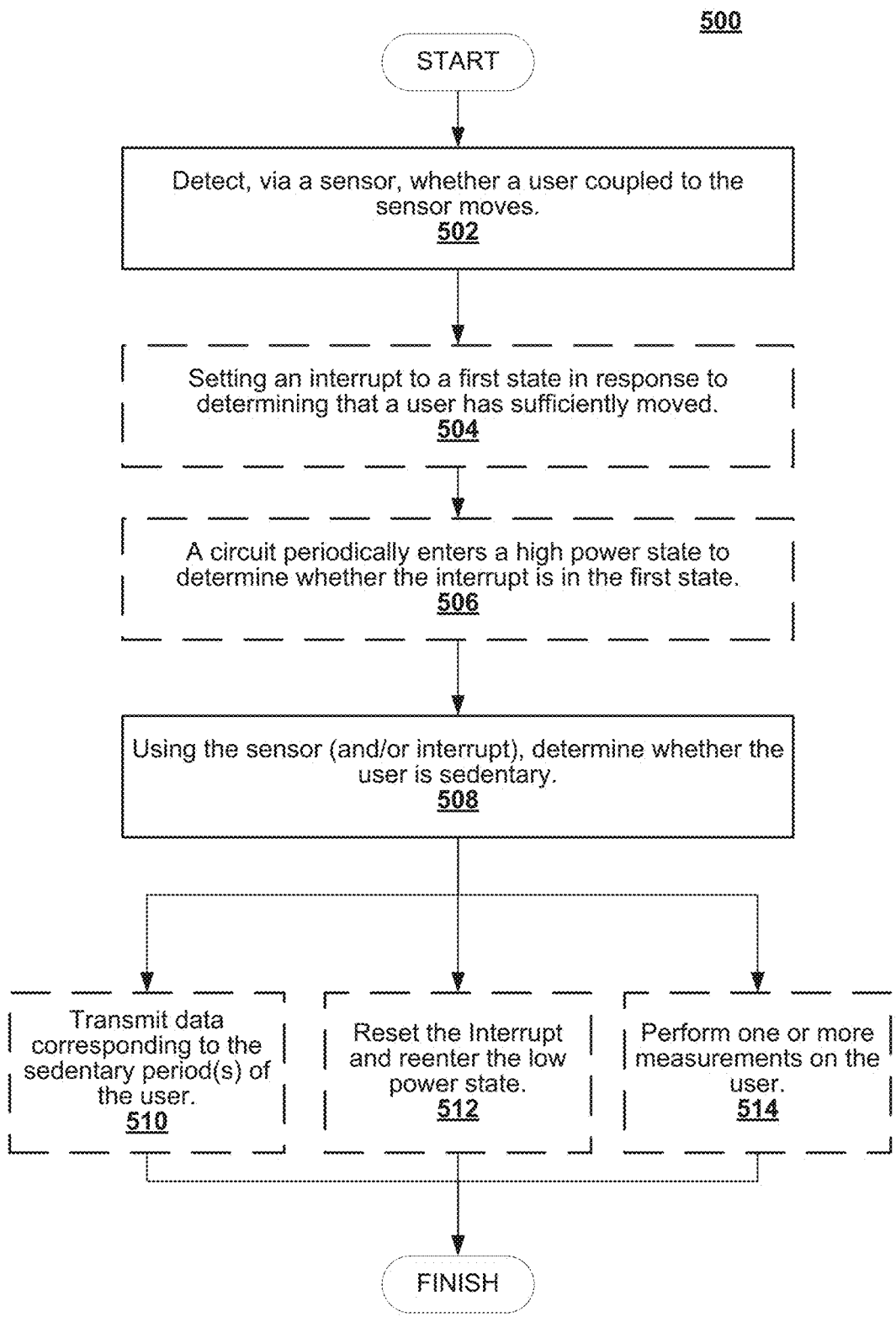
FIG. 5 illustrates an example flowchart describing features of the disclosure.

FIG. 5 illustrates an example flowchart 500 for implementing features of the disclosure. At 502, a sensor coupled to a user can be used to detect whether a user has moved. For example, sensor 104 can be coupled to user 114 via a fastener. When user 114 moves, sensor 104 can be used to output a corresponding signal indicative of movement of the user. At 504, an interrupt may be set to a first state in response to determining that the user has sufficiently moved, indicating that the movement has exceed a threshold used to determine whether the user is sedentary. The interrupt may be set independently of operations of a corresponding circuit. The interrupt can be a signal, a register, value, a mechanical component, etc.

At 506, a circuit can periodically enter a high power state to determine whether the interrupt is in the first state indicating that the user has not been sedentary. While in a low power state, the circuit use minimal power and may be unable to determine a state of the interrupt and/or perform action(s) in response to determine whether the interrupt is in the first state. At 508, while in a high power state, the circuit can determine whether the user is or has been sedentary. As disclosed, such a determination can be made by determining that the interrupt is in the second state, by comparing a current time with historic time(s) that the user has been sedentary, and/or by performing additional measurement(s) on the user which can be performed using additional sensor(s) to the one utilized to set the interrupt.

In response to determining whether the user is sedentary, several actions can be performed. For example, at 510, data can be transmitted corresponding to sedentary time period(s) of the user. For example, the circuit may log time periods that the user has been determined to be sedentary and send such information via a transceiver to a mobile device (such as mobile device 116). The data can be transmitted on command, at certain time periods, contemporaneously with the circuit being in a high power state, etc. At 512, the interrupt of 504 may be reset and the circuit may enter a low power state in response to determining that the user has not been sedentary, for example. Such actions may be performed in order to prevent psychological sensor reading from being performed with the user is active and may interfere with data gathering, for example. The circuit may, upon entering a high power state at a future time, determine whether the user is sedentary.

At 514, one or more measurements of physiological attribute(s) of a user may be measured, such as by the sensor used to determine whether the user is sedentary and/or additional sensors. The one or more measurements may be performed in response to determining that the user is sedentary, for example, and thus the one or more measurements can be performed with relatively less power and/or with relatively less interference than if the user were active.

Furthermore, the one or more measurements may desired to be collected specifically when the user is sedentary to aid in health assessment of the user, for example.

Figure 6:
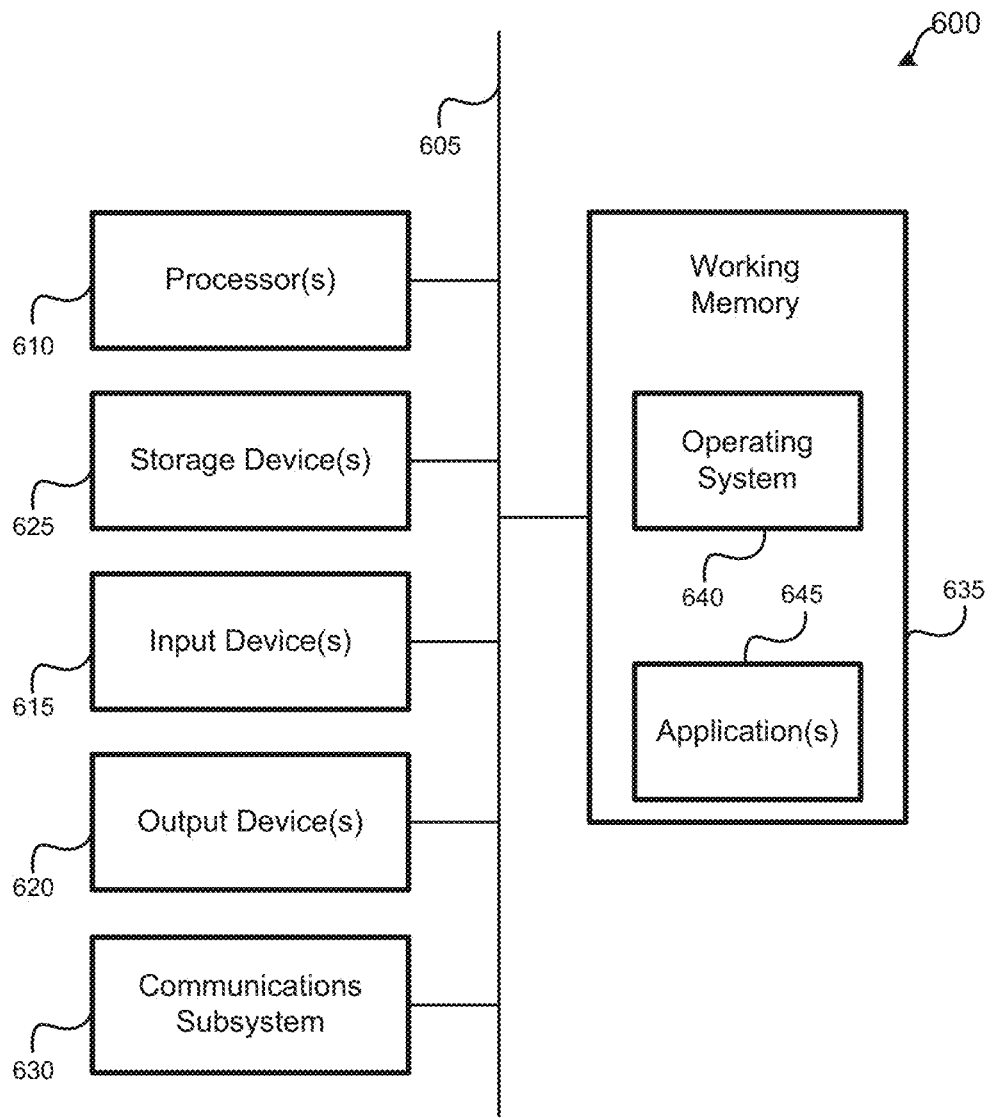
FIG. 6 illustrates an example of a computing system in which one or more embodiments may be implemented.

FIG. 6 illustrates an example computer system that can implement functionality of certain components, such as circuit 108. The computer system 600 is shown comprising hardware elements that can be electrically coupled via a bus 605 (or may otherwise be in communication, as appropriate). The hardware elements may include one or more processors 610, including without limitation one or more general-purpose processors and/or one or more special-purpose processors (such as digital signal processing chips, graphics acceleration processors, video decoders, and/or the like); one or more input devices 615, which can include without limitation a mouse, a keyboard, remote control, and/or the like; and one or more output devices 620, which can include without limitation a display device, a printer, and/or the like. As used herein, a controller can include functionality of a processor (such as processors 610).

The computer system 600 may further include (and/or be in communication with) one or more non-transitory storage devices 625, which can comprise, without limitation, local and/or network accessible storage, and/or can include, without limitation, a disk drive, a drive array, an optical storage device, a solid-state storage device, such as a random access memory ("RAM"), and/or a read-only memory ("ROM"), which can be programmable, flash-updateable and/or the like. Such storage devices may be configured to implement any appropriate data stores, including without limitation, various file systems, database structures, and/or the like.

The computer system 600 might also include a communications subsystem 630, which can include without limitation a modem, a network card (wireless or wired), an infrared communication device, a wireless communication device, and/or a chipset (such as a Bluetooth™ device, an 802.11 device, a Wi-Fi device, a WiMax device, cellular communication device, GSM, CDMA, WCDMA, LTE, LTE-A, LTE-U, etc.), and/or the like. The communications subsystem 630 may permit data to be exchanged with a network (such as the network described below, to name one example), other computer systems, and/or any other devices described herein. In many embodiments, the computer system 600 will further comprise a working memory 635, which can include a RAM or ROM device, as described above.

The computer system 600 also can comprise software elements, shown as being currently located within the working memory 635, including an operating system 640, device drivers, executable libraries, and/or other code, such as one or more application programs 645, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be stored on a non-transitory computer-readable storage medium, such as the non-transitory storage device(s) 625 described above. In some cases, the storage medium might be incorporated within a computer system, such as computer system 600. In other embodiments, the storage medium might be separate from a computer system (e.g., a removable medium, such as a compact disc), and/or provided in an installation package, such that the storage medium can be used to program, configure, and/or adapt a general purpose computer with the instructions/code stored thereon. These instructions might take the form of executable code, which is executable by the computer system 600 and/or might take the form of source and/or installable code, which, upon compilation and/or installation on the computer system 600 (e.g., using any of a variety of generally available compilers, installation programs, compression/decompression utilities, etc.), then takes the form of executable code.

It will be apparent to those skilled in the art that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

As mentioned above, in one aspect, some embodiments may employ a computer system (such as the computer system 600) to perform methods in accordance with various embodiments of the invention. According to a set of embodiments, some or all of the procedures of such methods are performed by the computer system 600 in response to processor 610 executing one or more sequences of one or more instructions (which might be incorporated into the operating system 640 and/or other code, such as an application program 645) contained in the working memory 635. Such instructions may be read into the working memory 635 from another computer-readable medium, such as one or more of the non-transitory storage device(s) 625. Merely by way of example, execution of the sequences of instructions contained in the working memory 635 might cause the processor(s) 610 to perform one or more procedures of the methods described herein.

The terms "machine-readable medium," "computer-readable storage medium" and "computer-readable medium," as used herein, refer to any medium that participates in providing data that causes a machine to operate in a specific fashion. These mediums may be non-transitory. In an embodiment implemented using the computer system 600, various computer-readable media might be involved in providing instructions/code to processor(s) 610 for execution and/or might be used to store and/or carry such instructions/code. In many implementations, a computer-readable medium is a physical and/or tangible storage medium. Such a medium may take the form of a non-volatile media or volatile media. Non-volatile media include, for example, optical and/or magnetic disks, such as the non-transitory storage device(s) 625. Volatile media include, without limitation, dynamic memory, such as the working memory 635.

Common forms of physical and/or tangible computer-readable media include, for example, a floppy disk, a flexible disk, hard disk, magnetic tape, or any other magnetic medium, a CD-ROM, any other optical medium, any other physical medium with patterns of marks, a RAM, a PROM, EPROM, a FLASH-EPROM, any other memory chip or cartridge, or any other medium from which a computer can read instructions and/or code.

Various forms of computer-readable media may be involved in carrying one or more sequences of one or more instructions to the processor(s) 610 for execution. Merely by way of example, the instructions may initially be carried on a magnetic disk and/or optical disc of a remote computer. A remote computer might load the instructions into its dynamic memory and send the instructions as signals over a transmission medium to be received and/or executed by the computer system 600.

The communications subsystem 630 (and/or components thereof) generally will receive signals, and the bus 605 then might carry the signals (and/or the data, instructions, etc. carried by the signals) to the working memory 635, from which the processor(s) 610 retrieves and executes the instructions. The instructions received by the working memory 635 may optionally be stored on a non-transitory storage device 625 either before or after execution by the processor(s) 610.

It should further be understood that the components of computer system 600 can be distributed across a network. For example, some processing may be performed in one location using a first processor while other processing may be performed by another processor remote from the first processor. Other components of computer system 600 may be similarly distributed. As such, computer system 600 may be interpreted as a distributed computing system that performs processing in multiple locations. In some instances, computer system 600 may be interpreted as a single computing device, such as a distinct laptop, desktop computer, or the like, depending on the context.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered.

Reference throughout this specification to "one example", "an example", "certain examples", or "exemplary implementation" means that a particular feature, structure, or characteristic described in connection with the feature and/or example may be included in at least one feature and/or example of claimed subject matter. Thus, the appearances of the phrase "in one example", "an example", "in certain examples" or "in certain implementations" or other like phrases in various places throughout this specification are not necessarily all referring to the same feature, example, and/or limitation. Furthermore, the particular features, structures, or characteristics may be combined in one or more examples and/or features.

Some portions of the detailed description included herein are presented in terms of algorithms or symbolic representations of operations on binary digital signals stored within a memory of a specific apparatus or special purpose computing device or platform. In the context of this particular specification, the term specific apparatus or the like includes a general purpose computer once it is programmed to perform particular operations pursuant to instructions from program software. Algorithmic descriptions or symbolic representations are examples of techniques used by those of ordinary skill in the signal processing or related arts to convey the substance of their work to others skilled in the art. An algorithm is here, and generally, is considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals, or the like. It should be understood, however, that all of these or similar terms are to be associated with appropriate physical quantities and are merely convenient labels. Unless specifically stated otherwise, as apparent from the discussion herein, it is appreciated that throughout this specification discussions utilizing terms such as "processing," "computing," "calculating," "determining" or the like refer to actions or processes of a specific apparatus, such as a special purpose computer, special purpose computing apparatus or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device.

Wireless communication techniques described herein may be in connection with various wireless communications networks such as a wireless wide area network ("WWAN"), a wireless local area network ("WLAN"), a wireless personal area network (WPAN), and so on. The term "network" and "system" may be used interchangeably herein. A WWAN may be a Code Division Multiple Access ("CDMA") network, a Time Division Multiple Access ("TDMA") network, a Frequency Division Multiple Access ("FDMA") network, an Orthogonal Frequency Division Multiple Access ("OFDMA") network, a Single-Carrier Frequency Division Multiple Access ("SC-FDMA") network, or any combination of the above networks, and so on. A CDMA network may implement one or more radio access technologies ("RATs") such as cdma2000, Wideband-CDMA ("W-CDMA"), to name just a few radio technologies. Here, cdma2000 may include technologies implemented according to IS-95, IS-2000, and IS-856 standards. A TDMA network may implement Global System for Mobile Communications ("GSM"), Digital Advanced Mobile Phone System ("D-AMPS"), or some other RAT. GSM and W-CDMA are described in documents from a consortium named "3rd Generation Partnership Project" ("3GPP"). Cdma2000 is described in documents from a consortium named "3rd Generation Partnership Project 2" ("3GPP2"). 3GPP and 3GPP2 documents are publicly available. 4G Long Term Evolution ("LTE") communications networks may also be implemented in accordance with claimed subject matter, in an aspect. A WLAN may comprise an IEEE 802.11x network, and a WPAN may comprise a Bluetooth network, an IEEE 802.15x, for example. Wireless communication implementations described herein may also be used in connection with any combination of WWAN, WLAN or WPAN.

In another aspect, as previously mentioned, a wireless transmitter or access point may comprise a cellular transceiver device, utilized to extend cellular telephone service into a business or home. In such an implementation, one or more mobile devices may communicate with a cellular transceiver device via a code division multiple access ("CDMA") cellular communication protocol, for example.

Techniques described herein may be used with an SPS that includes any one of several GNSS and/or combinations of GNSS. Furthermore, such techniques may be used with positioning systems that utilize terrestrial transmitters acting as "pseudolites", or a combination of SVs and such terrestrial transmitters. Terrestrial transmitters may, for example, include ground-based transmitters that broadcast a PN code or other ranging code (e.g., similar to a GPS or CDMA cellular signal). Such a transmitter may be assigned a unique PN code so as to permit identification by a remote receiver. Terrestrial transmitters may be useful, for example, to augment an SPS in situations where SPS signals from an orbiting SV might be unavailable, such as in tunnels, mines, buildings, urban canyons or other enclosed areas. Another implementation of pseudolites is known as radio-beacons. The term "SV", as used herein, is intended to include terrestrial transmitters acting as pseudolites, equivalents of pseudolites, and possibly others. The terms "SPS signals" and/or "SV signals", as used herein, is intended to include SPS-like signals from terrestrial transmitters, including terrestrial transmitters acting as pseudolites or equivalents of pseudolites.

In the preceding detailed description, numerous specific details have been set forth to provide a thorough understanding of claimed subject matter. However, it will be understood by those skilled in the art that claimed subject matter may be practiced without these specific details. In other instances, methods and apparatuses that would be known by one of ordinary skill have not been described in detail so as not to obscure claimed subject matter.

The terms, "and", "or", and "and/or" as used herein may include a variety of meanings that also are expected to depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein may be used to describe any feature, structure, or characteristic in the singular or may be used to describe a plurality or some other combination of features, structures or characteristics. Though, it should be noted that this is merely an illustrative example and claimed subject matter is not limited to this example.

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein.

Therefore, it is intended that claimed subject matter not be limited to the particular examples disclosed, but that such claimed subject matter may also include all aspects falling within the scope of appended claims, and equivalents thereof.

For an implementation involving firmware and/or software, the methodologies may be implemented with modules (e.g., procedures, functions, and so on) that perform the functions described herein. Any machine-readable medium tangibly embodying instructions may be used in implementing the methodologies described herein. For example, software codes may be stored in a memory and executed by a processor unit. Memory may be implemented within the processor unit or external to the processor unit. As used herein the term "memory" refers to any type of long term, short term, volatile, nonvolatile, or other memory and is not to be limited to any particular type of memory or number of memories, or type of media upon which memory is stored.

If implemented in firmware and/or software, the functions may be stored as one or more instructions or code on a computer-readable storage medium. Examples include computer-readable media encoded with a data structure and computer-readable media encoded with a computer program. Computer-readable media includes physical computer storage media. A storage medium may be any available medium that can be accessed by a computer. By way of example, and not limitation, such computer-readable media can comprise RAM, ROM, EEPROM, CD-ROM or other optical disk storage, magnetic disk storage, semiconductor storage, or other storage devices, or any other medium that can be used to store desired program code in the form of instructions or data structures and that can be accessed by a computer; disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

In addition to storage on computer-readable storage medium, instructions and/or data may be provided as signals on transmission media included in a communication apparatus. For example, a communication apparatus may include a transceiver having signals indicative of instructions and data. The instructions and data are configured to cause one or more processors to implement the functions outlined in the claims. That is, the communication apparatus includes transmission media with signals indicative of information to perform disclosed functions. At a first time, the transmission media included in the communication apparatus may include a first portion of the information to perform the disclosed functions, while at a second time the transmission media included in the communication apparatus may include a second portion of the information to perform the disclosed functions.

What is claimed is:

1. A device, comprising:
a fastener configured to attach the device to a user of the device;
a sensor coupled to the fastener, the sensor configured to collect readings of a movement of the user and to set an interrupt signal associated with the sensor to indicate a first state and a second state based on the collected readings, wherein the first state indicates that the collected readings are above a threshold and the second state indicates that the collected readings do not exceed the threshold, wherein the threshold comprises a magnitude threshold that is exceeded for a duration of time that exceeds a time threshold; and
a circuit coupled to the sensor, the circuit configured to operate in a low power state and a high power state independent of the interrupt signal of the sensor,
wherein when the circuit is operating in the low power state, the circuit ignores the readings of the sensor for sedentary determination;
wherein when the circuit enters the high power state at a first point in time independent of the interrupt signal of the sensor, the circuit is configured to determine whether the interrupt signal is in the first state or the second state;
in response to determining that the interrupt signal is in the first state, the circuit is configured to set the interrupt signal to the second state at the first point in time;
wherein when the circuit reenters the high power state at a second point in time after the first point in time independent of the interrupt signal of the sensor, the circuit is configured to determine whether the interrupt signal is in the first state or the second state; and
in response to determining that the interrupt signal is in the second state at the second point in time, the circuit is configured to:
determine, based on the collected readings, whether the user is sedentary; and
in response to determining that the user is sedentary, determine one or more physiological attributes of the user of the device.

2. The device of claim 1, wherein determining whether the user is sedentary includes determining whether a movement of the user detected by the sensor is within a threshold movement amount determined to indicate that the user is sedentary.

3. The device of claim 1, wherein determining whether the user is sedentary includes summing several movements over a time period to determine whether a resulting summation exceeds a corresponding threshold.

4. The device of claim 1, wherein the sensor includes an accelerometer or a gyroscope configured to detect whether the user has moved.

5. The device of claim 4, wherein determining that the user is sedentary includes determining that a magnitude of a translational or rotational force detected by the sensor corresponding to movement of the user has not met a threshold value.

6. The device of claim 5, wherein the sensor is configured to detect a combination of rotational and translational forces to determine whether a certain movement of the user has not been performed; and
the circuit is configured to determine, using the sensor, that the certain movement of the user has not been performed based on a comparison of multiple sensor signals corresponding to the rotational and translational forces to multiple respective thresholds during a time period.

7. The device of claim 1, wherein the one or more physiological attributes includes a heart rate, a breathing rate, or a galvanic skin response of the user.

8. The device of claim 1, wherein determining the one or more physiological attributes includes performing one or more measurements on the user.

9. The device of claim 8, wherein performing the one or more measurements includes inducing one or more sensors to enter a high power state from a low power state.

10. The device of claim 9, wherein the device includes the one or more sensors.

11. The device of claim 1, wherein the circuit is configured to: in response to determining that the user is sedentary, determine a length of time that the user has been sedentary.

12. The device of claim 1, wherein the circuit is configured to:
operate selectively in the low power state and the high power state, wherein the circuit is unable to determine whether the user is sedentary while in the low power state; and
periodically enter the high power state from the low power state to sample the readings from the sensor to determine whether the user is sedentary.

13. The device of claim 12, further comprising additional sensors configured to collect additional readings of the user;
wherein the circuit is configured to activate the additional sensors in response to determining that the interrupt signal has been set to the second state.

14. The device of claim 13, wherein the circuit is configured to, upon determining that the interrupt signal is set to the first state, set the interrupt signal to the second state and enter the low power state.

15. The device of claim 1, wherein determining that the user is sedentary includes:
determining that the readings have not exceeded the threshold for a pre-determined period of time.

16. The device of claim 1, wherein the fastener includes an adhesive to enable attachment of the device to the user.

17. The device of claim 1, comprising:
a power source coupled to the sensor and the circuit; and
a housing coupled to the sensor, the circuit, and the power source, wherein the housing is configured to prevent access to the power source without destructive deformation of the housing.

18. The device of claim 1, comprising:
a transmitter coupled to the circuit, wherein the circuit is configured to:
transmit data via the transmitter, the data indicative of the user being sedentary.

19. The device of claim 18, wherein the transmitter is a Bluetooth® or NIFC® compliant transmitter.

20. The device of claim 18, comprising:
a memory configured to store data indicative of several discontinuous periods of time that the user has been sedentary; and wherein the data transmitted via the transmitter includes the data indicative of several discontinuous periods of time that the user has been sedentary.

21. The device of claim 20, wherein the data indicative of several discontinuous periods of time that the user has been sedentary includes a time of day corresponding to each of the several discontinuous periods of time.

22. The device of claim 1, further comprising a register coupled with both the sensor and the circuit to store the interrupt signal.

23. The device of claim 1, wherein the circuit is configured to determine that the user is sedentary based on comparing a current time and one or more historic times when the user was sedentary.

24. The device of claim 1, wherein in response to determining that the interrupt signal is in the first state, the circuit is configured to activate one or more additional sensors to collect information regarding when the user is likely to be sedentary.

25. An apparatus, comprising:
a means to attach the apparatus to a user of the apparatus;
a means to collect readings of a movement of the user;
a means to set an interrupt signal associated with the sensor to indicate a first state and a second state based on the readings, wherein the first state indicates that the readings are above a threshold and the second state indicates that the readings do not exceed the threshold; and
a means to:
operate in a low power state and a high power state independent of the interrupt signal of the sensor, wherein when operating in the low power state, the means ignores the readings of the sensor for sedentary determination;
wherein when the means enters the high power state at a first point in time independent of the interrupt signal of the sensor, the means is configured to determine whether the interrupt signal is in the first state or the second state;
in response to determining that the interrupt signal is in the first state, the means is configured to set the interrupt signal to the second state at the first point in time;
wherein when the means reenters the high power state at a second point in time after the first point in time independent of the interrupt signal of the sensor, the means is configured to determine whether the interrupt signal is in the first state or the second state; and
in response to determining that the interrupt signal is in the second state at the second point in time, the means is configured to:
determine, based on the readings, that the user is sedentary; and
in response to determining that the user is sedentary, determine one or more physiological attributes of the user of the apparatus.

26. The apparatus of claim 25, further comprising means to:
operate selectively in the low power state or the high power state, wherein the means to determine is unable to sample the readings from the means to collect the readings while the means to determine is in the low power state; and
periodically enter the high power state from the low power state to sample the readings from the means to collect the readings in order to determine that the user is sedentary.

27. The apparatus of claim 26, further comprising:
additional means to collect additional readings of the movement of the user; and
means to activate the additional means to collect additional readings in response to determining that the interrupt signal has been set to the second state.

28. The apparatus of claim 27, further comprising means to, upon determining that the interrupt signal is set to the first state, set the interrupt signal to the second state and enter the low power state.

29. A method, comprising:
collecting, by a sensor attached to a user, readings of a movement of the user;
operating, by a circuit coupled to the sensor, in a low power state in which the circuit ignores the readings of the sensor for sedentary determination;
entering, by the circuit, a high power state independent of the readings of the sensor;
when in the high power state, sampling, by the circuit, at a first point in time, an interrupt signal associated with the sensor wherein the interrupt signal can be set by the sensor to a first state indicating that the readings are above a threshold and a second state indicating that the readings do not exceed the threshold, wherein the threshold comprises a magnitude threshold that is exceeded for a duration of time that exceeds a time threshold;
determining, by the circuit, that the interrupt signal is set to the first state;
setting, by the circuit, at the first point in time, the interrupt signal to the second state after determining that the interrupt signal is set to the first state;
reentering, by the circuit, at a second point in time after the first point in time, the high power state independent of the readings of the sensor after setting the interrupt signal to the second state;
determining, by the circuit when reentered in the high power state, that the interrupt signal is in the second state; and
in response to determining that the interrupt signal is in the second state:
determining, by the circuit whether the user is sedentary; and
in response to determining that the user is sedentary, determining, by the circuit, one or more physiological attributes of the user.

30. The method of claim 29, comprising:
operating by the circuit selectively in the low power state or the high power state, wherein the circuit is unable to sample the readings, from the sensor, indicative of movement of the user while in the low power state; and
periodically entering, by the circuit, the high power state from the low power state to sample the readings from the sensor to determine that the user is sedentary.

31. The method of claim 30, further comprising:
activating additional sensors to collect additional readings of the movement of the user in response to determining that the interrupt signal has been set to the second state.

32. The method of claim 31, comprising:
upon determining that the interrupt signal is set to the first state, setting the interrupt signal to the second state and entering the low power state.

33. One or more non-transitory computer readable media including instructions that, when executed by one or more processors, configure the one or more processors to:

operate in a low power state in which the one or more processors ignore readings of a movement of a user from a sensor for sedentary determination;

enter a high power state independent of the readings from the sensor;

when in the high power state at a first point in time, detect a state of an interrupt signal set by the sensor, wherein the interrupt signal is configured to indicate: (i) a first state when the readings are above a threshold; and (ii) a second state when the readings do not exceed the threshold, wherein the threshold comprises a magnitude threshold that is exceeded for a duration of time that exceeds a time threshold;

set the interrupt signal to the second state at the first point in time when the interrupt signal is detected to be in the first state;

when in the high power state at a second point in time after the first point in time, detect whether the interrupt signal set by the sensor indicates the first state or the second state; and in response to determining that the interrupt signal is in the second state at the second point in time:
determine, based on the readings, that the user was sedentary between the first and second points in time;
determine, based on the readings, that the user continues to be sedentary after the second point in time;
continue to operate in the high power state after the second point in time in response to determining that the user is sedentary; and
determine one or more physiological attributes of the user after the second point in time.

\* \* \* \* \*